US010226371B2

(12) United States Patent
Hollett et al.

(10) Patent No.: US 10,226,371 B2
(45) Date of Patent: Mar. 12, 2019

(54) DELIVERY SYSTEM HAVING STENT RETENTION STRUCTURE

(71) Applicant: Boston Scientific Scimed, Inc., Maple Grove, MN (US)

(72) Inventors: Andrew K. Hollett, Somerville, MA (US); Jacob A. Graham, Walnut Creek, CA (US); Gary J. Leanna, Holden, MA (US); John A. Griego, Blackstone, MA (US); John Lane, Manchester, NH (US); Michael D. Amos, Ayer, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 101 days.

(21) Appl. No.: 15/496,332

(22) Filed: Apr. 25, 2017

(65) Prior Publication Data
US 2017/0224510 A1    Aug. 10, 2017

Related U.S. Application Data

(63) Continuation of application No. 14/330,783, filed on Jul. 14, 2014, now Pat. No. 9,649,213, which is a
(Continued)

(51) Int. Cl.
| | |
|---|---|
| *A61F 2/06* | (2013.01) |
| *A61F 2/966* | (2013.01) |
| *A61M 25/01* | (2006.01) |
| *A61M 25/00* | (2006.01) |
| *A61F 2/04* | (2013.01) |

(Continued)

(52) U.S. Cl.
CPC .............. *A61F 2/966* (2013.01); *A61F 2/042* (2013.01); *A61F 2/94* (2013.01); *A61M 25/0082* (2013.01); *A61M 25/0102* (2013.01); *A61F 2002/041* (2013.01); *A61F 2002/8483* (2013.01); *A61F 2002/9505* (2013.01); *A61F 2220/0016* (2013.01); *A61M 2025/0096* (2013.01)

(58) Field of Classification Search
CPC .. A61F 2/95; A61F 2/962; A61F 2/966; A61F 2/94; A61F 2/042; A61F 2002/041
See application file for complete search history.

(56) References Cited

U.S. PATENT DOCUMENTS 5,372,600 A * 12/1994 Beyar ...................... A61F 2/95
   606/194
5,824,041 A * 10/1998 Lenker .................... A61F 2/07
   606/195

(Continued)

*Primary Examiner* — Wade Miles

(57) ABSTRACT

A drainage stent delivery system including an elongate shaft of a medial device, a drainage catheter or stent, and an interference fit member for selectively coupling the drainage stent to the elongate shaft. The drainage stent is selectively coupled to a distal portion of the elongate shaft by an interference fit between the interference fit member and the drainage stent such that axial movement of the elongate shaft relative to the drainage stent moves the interference fit member from a first position in which the interference fit member is engaged with the drainage stent and forms an interference fit with the drainage stent to a second position in which the interference fit member is disengaged from the drainage stent.

15 Claims, 12 Drawing Sheets

Related U.S. Application Data continuation of application No. 13/157,401, filed on Jun. 10, 2011, now Pat. No. 8,808,348.

(60) Provisional application No. 61/357,742, filed on Jun. 23, 2010.

(51) Int. Cl.
*A61F 2/94* (2013.01)
*A61F 2/848* (2013.01)
*A61F 2/95* (2013.01)

(56) References Cited

U.S. PATENT DOCUMENTS

| | | | | |
|---|---|---|---|---|
| 5,871,537 | A * | 2/1999 | Holman | A61B 17/12045 606/194 |
| 6,368,344 | B1 * | 4/2002 | Fitz | A61F 2/95 606/108 |
| 8,133,265 | B2 * | 3/2012 | Seemann | A61F 2/95 623/1.11 |
| 8,211,087 | B2 * | 7/2012 | Carter | A61B 1/018 604/164.13 |
| 8,808,348 | B2 * | 8/2014 | Hollett | A61F 2/94 623/1.11 |
| 9,649,213 | B2 * | 5/2017 | Hollett | A61F 2/94 |
| 2002/0016597 | A1 * | 2/2002 | Dwyer | A61F 2/95 606/108 |
| 2003/0114910 | A1 * | 6/2003 | Juhani Laakso | A61F 2/95 623/1.11 |
| 2005/0085891 | A1 * | 4/2005 | Goto | A61F 2/94 623/1.11 |
| 2005/0085892 | A1 * | 4/2005 | Goto | A61F 2/94 623/1.12 |
| 2005/0090887 | A1 * | 4/2005 | Pryor | A61F 2/95 623/1.11 |
| 2005/0165352 | A1 * | 7/2005 | Henry | A61F 2/95 604/108 |
| 2006/0155359 | A1 * | 7/2006 | Watson | A61F 2/07 623/1.13 |
| 2006/0276873 | A1 * | 12/2006 | Sato | A61B 17/3468 623/1.11 |
| 2007/0005122 | A1 * | 1/2007 | Inoue | A61F 2/94 623/1.11 |
| 2007/0293929 | A1 * | 12/2007 | Aoba | A61F 2/95 623/1.11 |
| 2009/0143849 | A1 * | 6/2009 | Ozawa | A61F 2/94 623/1.11 |
| 2009/0312829 | A1 * | 12/2009 | Aoba | A61F 2/94 623/1.11 |
| 2010/0137966 | A1 * | 6/2010 | Magnuson | A61F 2/95 623/1.11 |
| 2011/0160739 | A1 * | 6/2011 | Amos | A61M 25/0662 606/108 |
| 2012/0095567 | A1 * | 4/2012 | Weisman | A61F 2/95 623/23.7 |

* cited by examiner

DELIVERY SYSTEM HAVING STENT RETENTION STRUCTURE

CROSS REFERENCE TO RELATED APPLICATIONS

This application is a continuation of U.S. patent application Ser. No. 14/330,783, filed on Jul. 14, 2014, now granted as U.S. Pat. No. 9,649,213, which is a continuation of U.S. patent application Ser. No. 13/157,401, filed Jun. 10, 2011, now granted as U.S. Pat. No. 8,808,348, which claims the benefit of U.S. Provisional Application Ser. No. 61/357,742, filed Jun. 23, 2010, the entire disclosures of which are incorporated herein by reference.

TECHNICAL FIELD

The disclosure is directed to a retention structure of a medical device. More particularly, the disclosure is directed to a stent retention structure for selectively securing a stent to a shaft of a stent delivery system. Specifically, the disclosure is directed to a retention structure for selectively securing a drainage stent to a catheter shaft of a drainage stent delivery system.

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a retention system to releasably secure a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a retention structure for selectively securing a stent to a delivery system.

Accordingly, one illustrative embodiment is a stent delivery system comprising an elongate shaft of a medical device, a tubular stent positioned on and surrounding a distal portion of the elongate shaft, and an interference fit member positioned on the elongate shaft and configured to cooperate with the tubular stent to form an interference fit therebetween. Axial movement of the elongate shaft relative to the tubular stent moves the interference fit member from a first position in which the interference fit member is positioned within the lumen of the tubular stent and forms an interference fit with the tubular stent to a second position in which the interference fit member is positioned exterior of the lumen of the tubular stent.

Another illustrative embodiment is a drainage stent delivery system including a drainage stent including a generally non-expandable tubular member having a proximal end, a distal end and a central longitudinal axis. The drainage stent delivery system also includes an elongate shaft extending distally from a handle assembly to a location distal of the proximal end of the drainage stent. The elongate shaft includes a portion configured to form an interference fit with the drainage stent. The elongate shaft is longitudinally moveable relative to the drainage stent to effect disengagement of the drainage stent from the portion of the elongate shaft configured to form an interference fit with the drainage stent.

Yet another illustrative embodiment is a method of selectively releasing a stent from an elongate shaft of a medical device. The method includes positioning a tubular stent removably coupled to a distal portion of an elongate shaft of a medical device at a target location of an anatomy. The tubular stent is removably coupled to the distal portion of the elongate shaft by an interference fit between the tubular stent and an interference fit portion of the elongate shaft. The elongate shaft may be moved in an axial direction relative to the tubular stent to disengage the tubular stent from the interference fit portion of the elongate shaft.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
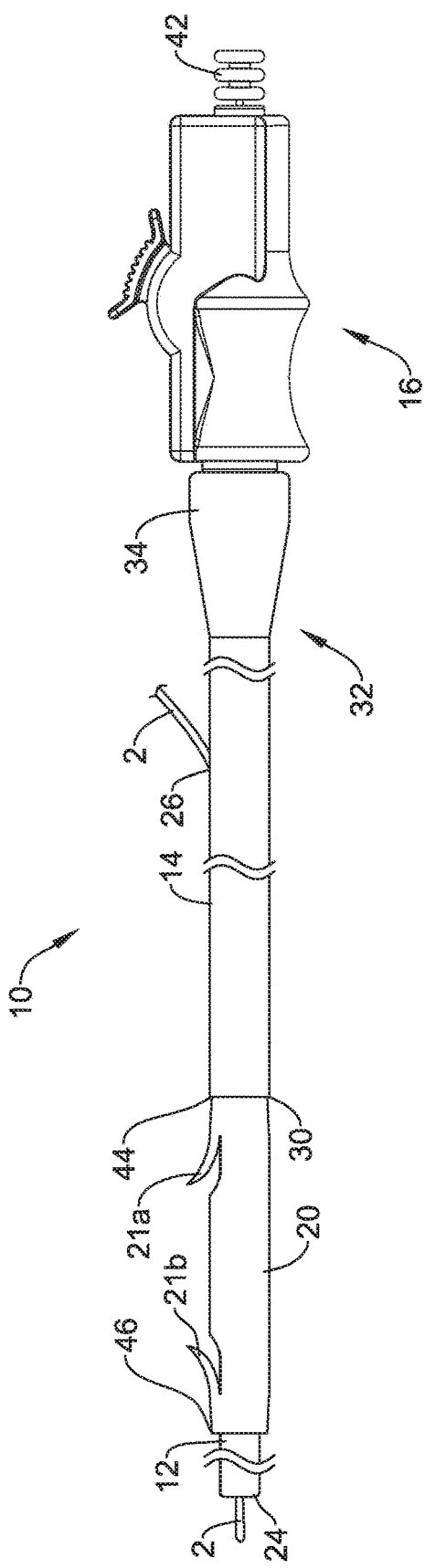
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
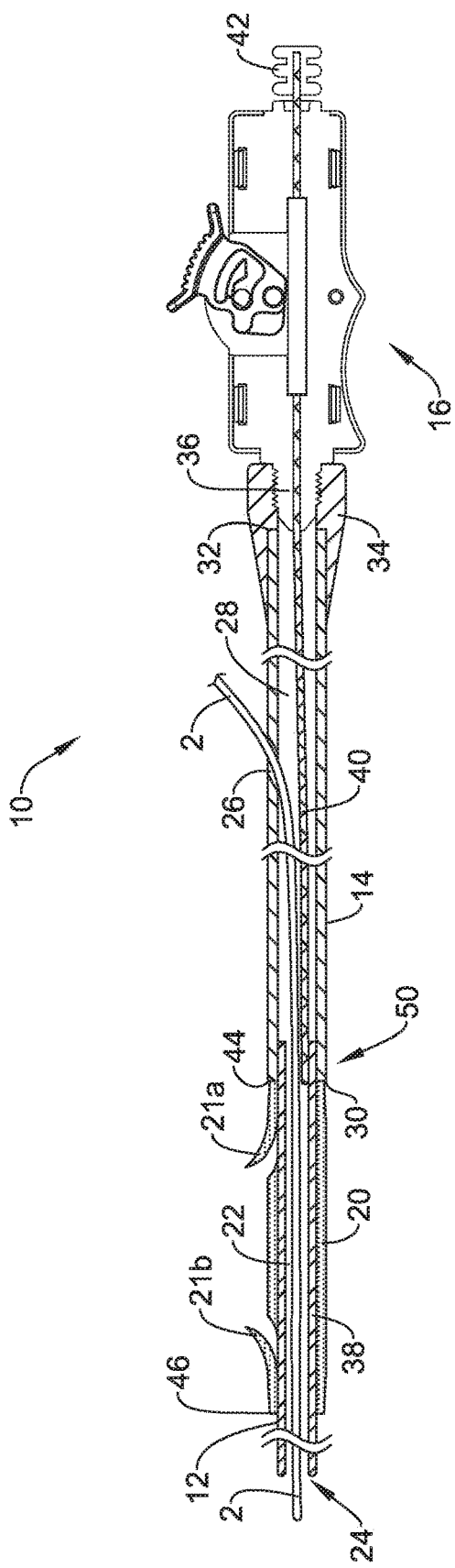
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. The drainage stent 20 may be an elongate tubular member which is generally not expandable. The drainage stent 20 may have a proximal end 44, a distal end 46 and a lumen 48 extending through the drainage stent 20 from the proximal end 44 to the distal end 46. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage stent delivery system 10 with single-operator-exchange (SOE) capabilities.

The guide catheter 12 may be slidably disposed in the lumen 28 of the push catheter 14 and extend distally from the distal end 30 of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end of the drainage stent 20 may abut and/or face a distal end or rim 30 of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The drainage stent delivery system 10 may include a means for releasably connecting the drainage stent 20 to an elongate shaft of the drainage stent delivery system 10, such as the guide catheter 12 or the push catheter 14 of the drainage stent delivery system 10. When the drainage stent 20 has been properly placed, the drainage stent 20 may be disconnected from the drainage stent delivery system 10 such that the drainage stent 20 remains in the lumen when the guide catheter 12 and/or the push catheter 14 are withdrawn. Some exemplary retention mechanisms for selectively coupling the drainage stent 20 to an elongate shaft of the drainage stent delivery system 10 are further described herein. The retention mechanisms may be used to selectively deploy, reposition and/or retrieve the drainage stent 20 during a medical procedure.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location. The elongate wire 40 may extend through the lumen 28 of the push catheter 14 to the handle assembly 16 while the distal tubular portion 38 extends through the drainage stent 20 to a location distal of the drainage stent 20. In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments axial movement of an elongate shaft of the drainage stent delivery system 10 (e.g., the guide catheter 12 and/or the push catheter 14) relative to the drainage stent 20 may disengage or unlock the drainage stent 20 from the drainage stent delivery system 10. Once the drainage stent 20 is disengaged from the guide catheter 12 and/or the push catheter 14, withdrawing the guide catheter 12 and/or the push catheter 14 proximally may release the drainage stent 20 from the drainage stent delivery system 10 in order to deploy the drainage stent 20 at the target location. Once the drainage stent 20 has been properly deployed at the target location, the drainage stent delivery system 10 may then be withdrawn. In some instances, the drainage stent delivery system 10 may also be used to reposition and/or retrieve the drainage stent 20 during a medical procedure.

Some exemplary retention structures for selectively coupling the drainage stent 20 to a component, such as an elongate shaft, of the drainage stent delivery system 10 will now be further described.

Figure 3A:
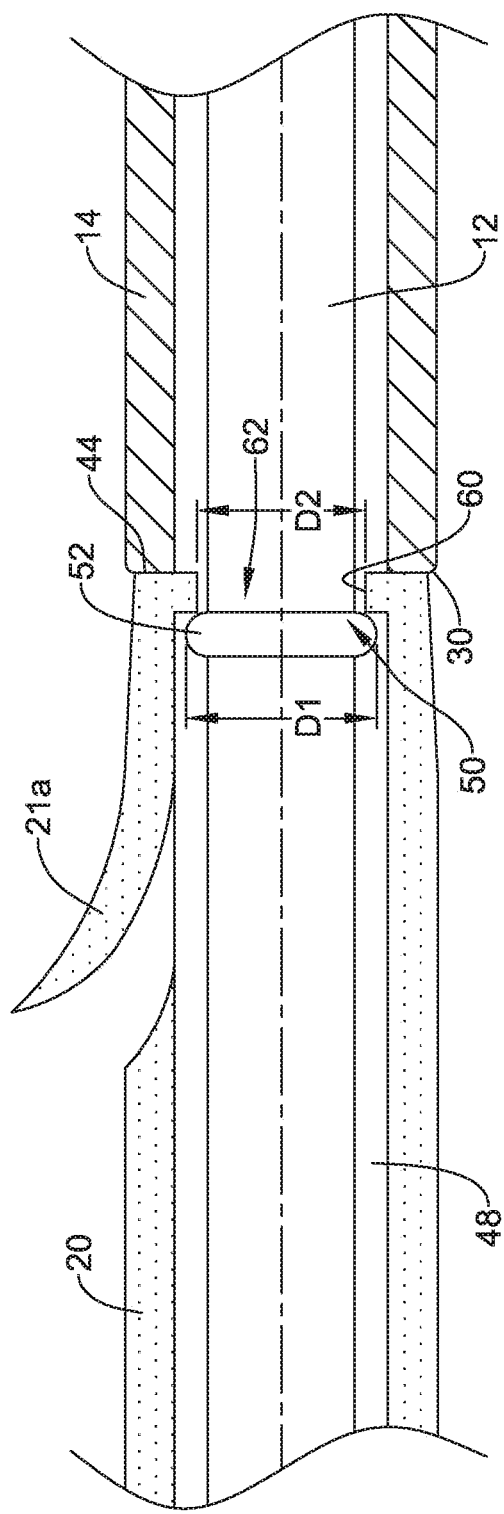
FIGS. 3A and 3B are longitudinal cross-sectional views illustrating the functionality of an exemplary retention structure for selectively coupling a stent to an elongate shaft of a delivery system.
Figure 3B:
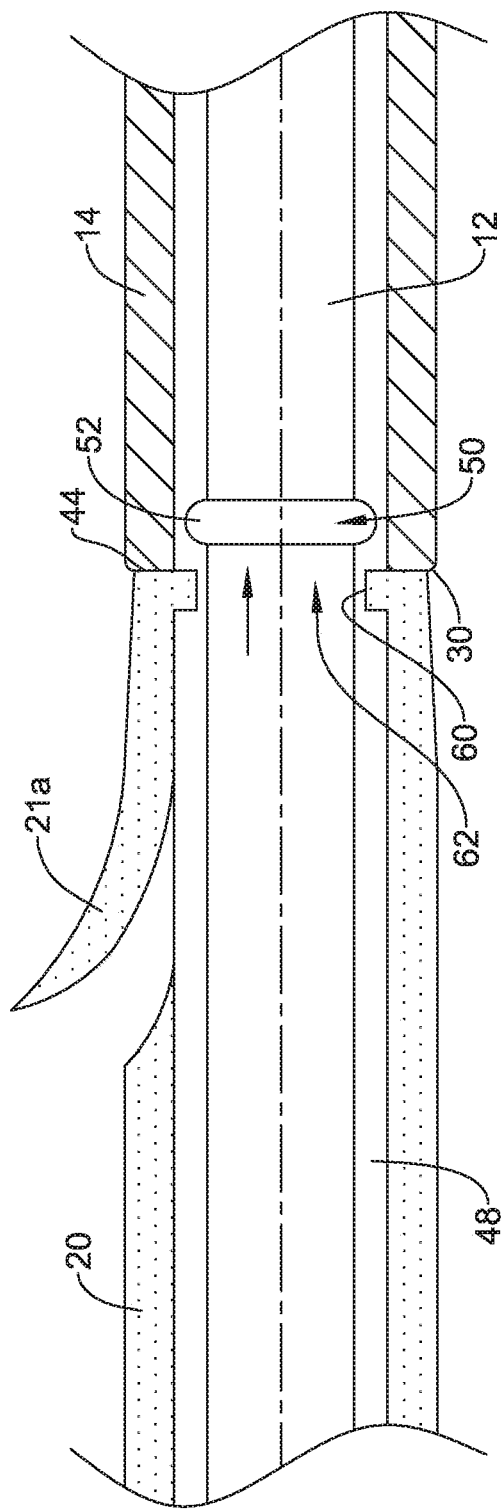

FIGS. 3A and 3B illustrate the functionality of a first exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 3A and 3B.

FIG. 3A illustrates the drainage stent 20 positioned on and surrounding the elongate shaft of the guide catheter 12 in which the drainage stent 20 is retained on the guide catheter 12. As shown in FIG. 3A, a distal portion of the guide catheter 12 may extend distally from the distal end 30 of the push catheter 14 into and/or through the lumen 48 of the drainage stent 20 such that the distal end of the guide catheter 12 is located distal of the proximal end 44 of the drainage stent 20.

The guide catheter 12 may include a portion configured to form an interference fit with the drainage stent 20. For instance, the guide catheter 12 may include an interference fit member 50 positioned on the elongate shaft of the guide catheter 12. The interference fit member 50 may be configured to cooperate with the drainage stent 20 to form an interference fit therebetween. In some instances, as shown in FIG. 3A, the interference fit member 50 may be a raised protuberance 52 extending radially outward from the outer surface of the elongate shaft of the guide catheter 12. In some instances, the protuberance 52 may be an annular ridge extending circumferentially around the elongate shaft of the guide catheter 12. In other instances, the protuberance 52 may be one or more bumps, projections, bulges or other features extending radially outward of the outer surface of the elongate shaft of the guide catheter 12. The protuberance 52 may be a unitary portion of the elongate shaft of the guide catheter 12 or the protuberance 52 may be a separate component secured to the elongate shaft of the guide catheter 12.

The protuberance 52 may be configured to form an interference fit with a portion of the drainage stent 20 to selectively retain the drainage stent 20 on the guide catheter 12 until deployment of the drainage stent 20 is desired. For example, the protuberance 52 may be configured to be in contact with an interior surface of the drainage stent 20, forming an interference fit therebetween. As shown in FIG. 3A, the drainage stent 20 may include a radially inward extending lip 60 at the proximal end 44 of the drainage stent 20. The lip 60 may define an opening 62 into the interior of the drainage stent 20 through which the guide catheter 12 extends through. The opening 62 may have a diameter D2 which is less than the inner diameter of the more distal portion of the drainage stent 20. The diameter D2 of the opening 62 may be less than the radial extent or diameter D1 of the protuberance 52, creating an interference fit between the protuberance 52 and the lip 60.

With the protuberance 52 on the elongate shaft of the guide catheter 12 located in a first position, shown in FIG. 3A, in which the protuberance 52 is positioned within the lumen 48 of the drainage stent 20, the drainage stent 20 is secured to the guide catheter 12. The interference fit between the protuberance 52 and the lip 60 prevents decoupling of the drainage stent 20 from the guide catheter 12 without applying a threshold amount of force to overcome the interference fit. In some instances, the lip 60 of the drainage stent 20 may be interposed between the distal end 30 of the push catheter 14 and the protuberance 52 on the guide catheter 12 when the drainage stent 20 is removably coupled to the drainage stent delivery system 10.

The drainage stent 20 may be decoupled from the guide catheter 12 through axial movement of the guide catheter 12 relative to the drainage stent 20 while the proximal end 44 of the drainage stent 20 abuts the distal end 30 of the push catheter 14, holding the drainage stent 20 stationary relative to the push catheter 14. For instance, as shown in FIG. 3B, axial or longitudinal movement of the guide catheter 12 in a proximal direction may move the protuberance 52 from the first position in which the protuberance 52 is positioned within the lumen 48 of the drainage stent 20 to a second position in which the protuberance 52 is positioned exterior of the lumen 48 of the drainage stent 20, for example, proximal of the drainage stent 20.

An axial force greater than a threshold level is necessary to deflect the protuberance 52 and/or the lip 60 of the drainage stent 20 a sufficient amount to allow the protuberance 52 to be pulled proximally out through the opening 62 of the drainage stent 20. For instance, the protuberance 52 and/or the lip 60 may be sized and configured such that an axial force of less than 2 pounds applied to the guide catheter 12 is insufficient to pull the protuberance 52 proximally through the opening 62 of the drainage stent 20. The protuberance 52 and/or the lip 60 may be sized and configured such that an axial force greater than 2 pounds, for example, an axial force of about 3 pounds to about 4 pounds, may be sufficient to deflect the protuberance 52 and/or the lip 60 of the drainage stent 20 to allow the protuberance 52 to be removed from the interior of the drainage stent 20. The threshold level of force needed to withdraw the protuberance 52 from the lumen 48 of the drainage stent 20, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, axial force applied to the guide catheter 12 pushes the proximal end 44 of the drainage stent 20 into contact with the distal end 30 of the push catheter 14 as the protuberance 52 pushes against the distal side of the lip 60. When a sufficient axial force is applied, the protuberance 52 is pulled through the opening 62 of the drainage stent 20. Thus, the axial force applied to withdraw the guide catheter 12 from the drainage stent 20 must be sufficiently large to deflect the protuberance 52 and/or the lip 60 sufficiently to allow the protuberance 52 to pass through the opening 62.

Figure 4A:
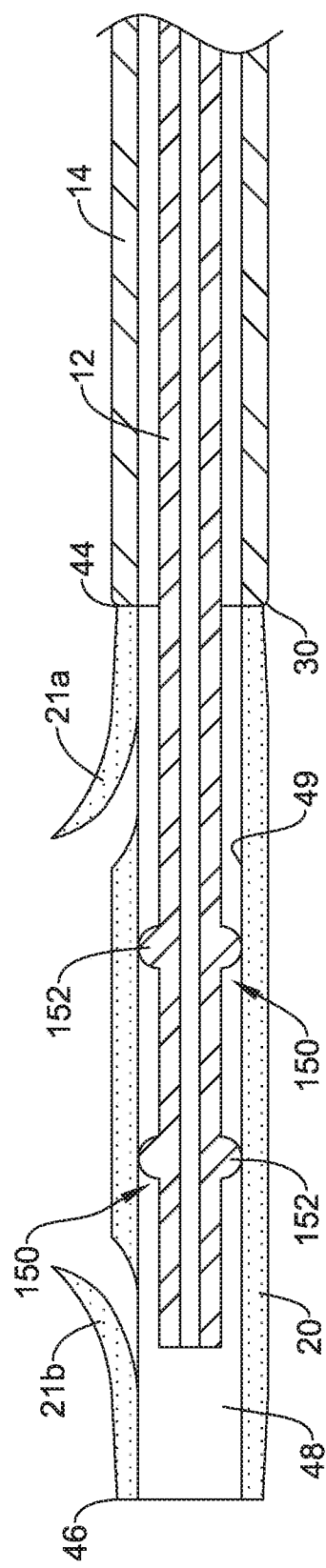
FIGS. 4A and 4B are longitudinal cross-sectional views illustrating the functionality of another retention structure for selectively coupling a stent to an elongate shaft of a delivery system.
Figure 4B:
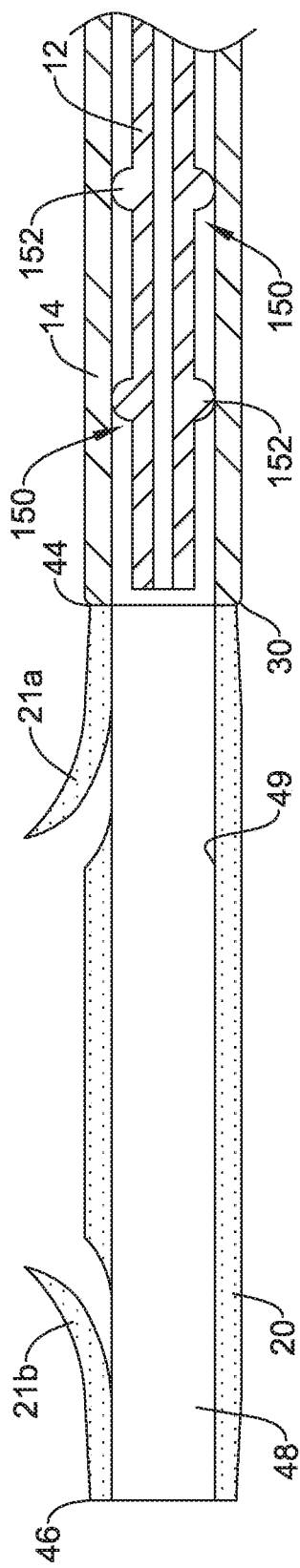

FIGS. 4A and 4B illustrate the functionality of a second exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 4A and 4B.

FIG. 4A illustrates the drainage stent 20 positioned on and surrounding the elongate shaft of the guide catheter 12 in which the drainage stent 20 is retained on the guide catheter 12. As shown in FIG. 4A, a distal portion of the guide catheter 12 may extend distally from the distal end 30 of the push catheter 14 into and/or through the lumen 48 of the drainage stent 20 such that the distal end of the guide catheter 12 is located distal of the proximal end 44 of the drainage stent 20.

The guide catheter 12 may include a portion configured to form an interference fit with the drainage stent 20. For instance, the guide catheter 12 may include an interference fit member 150 (or a plurality of interference fit members) positioned on the elongate shaft of the guide catheter 12. The interference fit member 150 may be configured to cooperate with the drainage stent 20 to form an interference fit therebetween. In some instances, as shown in FIG. 4A, the interference fit member 150 may be a raised protuberance 152, or a plurality of raised protuberances 152, extending radially outward from the outer surface of the elongate shaft of the guide catheter 12. In some instances, the protuberance(s) 152 may be an annular ridge extending circumferentially around the elongate shaft of the guide catheter 12. In other instances, the protuberance(s) 152 may be one or more bumps, projections, bulges or other features extending radially outward of the outer surface of the elongate shaft of the guide catheter 12. The protuberance(s) 152 may be a unitary portion of the elongate shaft of the guide catheter 12 or the protuberance(s) 152 may be a separate component secured to the elongate shaft of the guide catheter 12.

While further discussion will be directed to a protuberance 152 of the guide catheter 12, it is noted that the discussion may apply equality to each protuberance 152 of the guide catheter 12. The protuberance 152 may be configured to form an interference fit with a portion of the drainage stent 20 to selectively retain the drainage stent 20 on the guide catheter 12 until deployment of the drainage stent 20 is desired. For example, the protuberance 152 may be configured to be in contact with an interior surface 49 of the drainage stent 20, forming an interference fit therebetween. For instance, the interference fit may be a frictional fit between the surface of the protuberance 152 and the interior surface 49 of the drainage stent 20 having a coefficient of static friction sufficient to retain the drainage stent 20 on the guide catheter 12 until deployment is desired.

With the protuberance 152 on the elongate shaft of the guide catheter 12 located in a first position, shown in FIG. 4A, in which the protuberance 152 is positioned within the lumen 48 of the drainage stent 20, the drainage stent 20 is secured to the guide catheter 12. The interference frictional fit between the protuberance 152 and the interior surface 49 of the drainage stent 20 prevents decoupling of the drainage stent 20 from the guide catheter 12 without applying a threshold amount of force to overcome the interference fit.

The drainage stent 20 may be decoupled from the guide catheter 12 through axial movement of the guide catheter 12 relative to the drainage stent 20 while the proximal end 44 of the drainage stent 20 abuts the distal end 30 of the push catheter 14, holding the drainage stent 20 stationary relative to the push catheter 14. For instance, as shown in FIG. 4B, axial or longitudinal movement of the guide catheter 12 in a proximal direction may move the protuberance(s) 152 from the first position in which the protuberance(s) 152 is/are positioned within the lumen 48 of the drainage stent 20 to a second position in which the protuberance(s) 152 is/are positioned exterior of the lumen 48 of the drainage stent 20, for example, proximal of the drainage stent 20.

An axial force greater than a threshold level is necessary to overcome the coefficient of static friction caused by the interference frictional fit between the protuberance(s) 152 and the interior surface 49 of the drainage stent 20 a sufficient amount to allow the protuberance(s) 152 to be pulled proximally out of the lumen 48 of the drainage stent 20 to a position proximal of the drainage stent 20. For instance, the protuberance(s) 152 may be sized and configured relative to the inner diameter of the drainage stent 20 such that an axial force of less than 2 pounds applied to the guide catheter 12 is insufficient to pull the protuberance(s) 152 proximally from the lumen 48 of the drainage stent 20. The protuberance(s) 152 may be sized and configured such that an axial force greater than 2 pounds, for example, an axial force of about 3 pounds to about 4 pounds, may be sufficient to overcome the coefficient of static friction between the protuberance(s) 152 and the interior surface 49 of the drainage stent 20 to allow the protuberance(s) 152 to be removed from the interior of the drainage stent 20. The threshold level of force needed to withdraw the protuberance(s) 152 from the lumen 48 of the drainage stent 20, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, axial force applied to the guide catheter 12 pushes the proximal end 44 of the drainage stent 20 into contact with the distal end 30 of the push catheter 14 as the protuberance(s) 152 is frictionally engaged and stationary with the drainage stent 20. When a sufficient axial force is applied to overcome the static frictional force between the protuberance(s) 152 and the drainage stent 20, the protuberance(s) 152 is/are pulled proximally relative to the drainage stent 20 to a position proximal of the drainage stent 20. Thus, the axial force applied to withdraw the guide catheter 12 from the drainage stent 20 must be sufficiently large to overcome the static frictional forces caused by the interference fit between the protuberance(s) 152 and the interior surface 49 of the drainage stent 20.

Figure 5A:
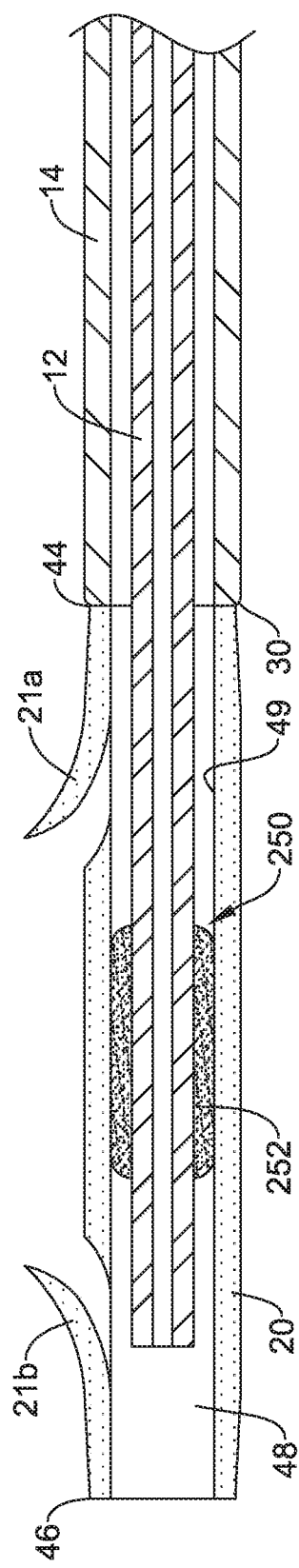
FIGS. 5A and 5B are longitudinal cross-sectional views illustrating the functionality of another retention structure for selectively coupling a stent to an elongate shaft of a delivery system.
Figure 5B:
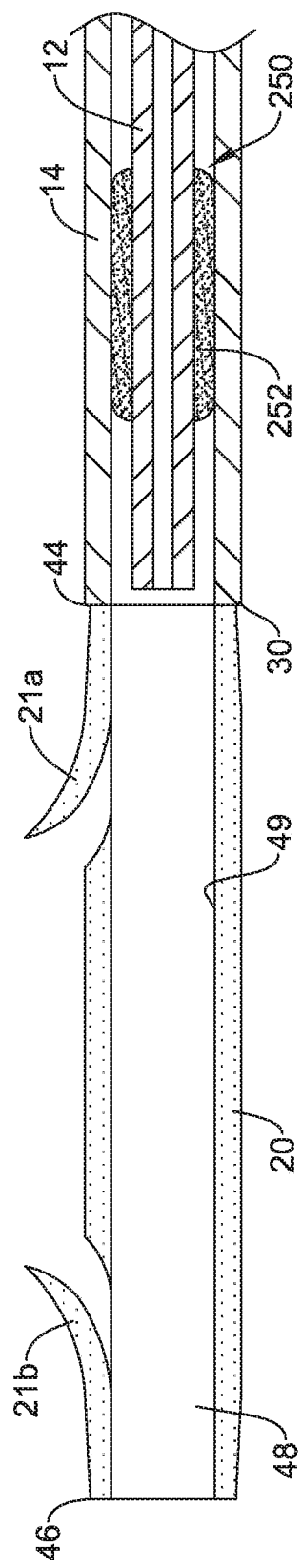

FIGS. 5A and 5B illustrate the functionality of another exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 5A and 5B.

FIG. 5A illustrates the drainage stent 20 positioned on and surrounding the elongate shaft of the guide catheter 12 in which the drainage stent 20 is retained on the guide catheter 12. As shown in FIG. 5A, a distal portion of the guide catheter 12 may extend distally from the distal end 30 of the push catheter 14 into and/or through the lumen 48 of the drainage stent 20 such that the distal end of the guide catheter 12 is located distal of the proximal end 44 of the drainage stent 20.

The guide catheter 12 may include a portion configured to form an interference fit with the drainage stent 20. For instance, the guide catheter 12 may include an interference fit member 250 positioned on the elongate shaft of the guide catheter 12. The interference fit member 250 may be configured to cooperate with the drainage stent 20 to form an interference fit therebetween. In some instances, as shown in FIG. 5A, the interference fit member 250 may be an annular sleeve 252 circumferentially surrounding the outer surface of the elongate shaft of the guide catheter 12. In some instances, the annular sleeve 252 may be formed of a polymeric foam material or other compressible material.

The annular sleeve 252 may be configured to form an interference fit with a portion of the drainage stent 20 to selectively retain the drainage stent 20 on the guide catheter 12 until deployment of the drainage stent 20 is desired. For example, the annular sleeve 252 may be configured to be in contact with an interior surface 49 of the drainage stent 20, forming an interference fit therebetween. For instance, the interference fit may be a frictional fit between the surface of the annular sleeve 252 and the interior surface 49 of the drainage stent 20 having a coefficient of static friction sufficient to retain the drainage stent 20 on the guide catheter 12 until deployment is desired. The annular sleeve 252, which may comprise a compressible material, such as a polymeric foam, may be radially compressed when positioned in the lumen 48 of the drainage stent 20.

With the annular sleeve 252 on the elongate shaft of the guide catheter 12 located in a first position, shown in FIG. 5A, in which the annular sleeve 252 is positioned within the lumen 48 of the drainage stent 20, the drainage stent 20 is secured to the guide catheter 12. Compression of the annular sleeve 252 against the interior surface 49 of the drainage stent 20 provides an interference frictional fit. The interference frictional fit between the annular sleeve 252 and the interior surface 49 of the drainage stent 20 prevents decoupling of the drainage stent 20 from the guide catheter 12 without applying a threshold amount of force to overcome the interference fit.

The drainage stent 20 may be decoupled from the guide catheter 12 through axial movement of the guide catheter 12 relative to the drainage stent 20 while the proximal end 44 of the drainage stent 20 abuts the distal end 30 of the push catheter 14, holding the drainage stent 20 stationary relative to the push catheter 14. For instance, as shown in FIG. 5B, axial or longitudinal movement of the guide catheter 12 in a proximal direction may move the annular sleeve 252 from the first position in which the annular sleeve 252 is positioned within the lumen 48 of the drainage stent 20 to a second position in which the annular sleeve 252 is positioned exterior of the lumen 48 of the drainage stent 20, for example, proximal of the drainage stent 20.

An axial force greater than a threshold level is necessary to overcome the coefficient of static friction caused by the interference frictional fit between the annular sleeve 252 and the interior surface 49 of the drainage stent 20 a sufficient amount to allow the annular sleeve 252 to be pulled proximally out of the lumen 48 of the drainage stent 20 to a position proximal of the drainage stent 20. For instance, the annular sleeve 252 may be sized and configured relative to the inner diameter of the drainage stent 20 such that an axial force of less than 2 pounds applied to the guide catheter 12 is insufficient to pull the annular sleeve 252 proximally from the lumen 48 of the drainage stent 20. The annular sleeve 252 may be sized and configured such that an axial force greater than 2 pounds, for example, an axial force of about 3 pounds to about 4 pounds, may be sufficient to overcome the coefficient of static friction between the annular sleeve 252 and the interior surface 49 of the drainage stent 20 to allow the annular sleeve 252 to be removed from the interior of the drainage stent 20. The threshold level of force needed to withdraw the annular sleeve 252 from the lumen 48 of the drainage stent 20, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, axial force applied to the guide catheter 12 pushes the proximal end 44 of the drainage stent 20 into contact with the distal end 30 of the push catheter 14 as the annular sleeve 252 is frictionally engaged and stationary with the drainage stent 20. When a sufficient axial force is applied to overcome the static frictional force between the annular sleeve 252 and the drainage stent 20, the annular sleeve 252 is pulled proximally relative to the drainage stent 20 to a position proximal of the drainage stent 20. Thus, the axial force applied to withdraw the guide catheter 12 from the drainage stent 20 must be sufficiently large to overcome the static frictional forces caused by the interference fit between the annular sleeve 252 and the interior surface 49 of the drainage stent 20.

Figure 6A:
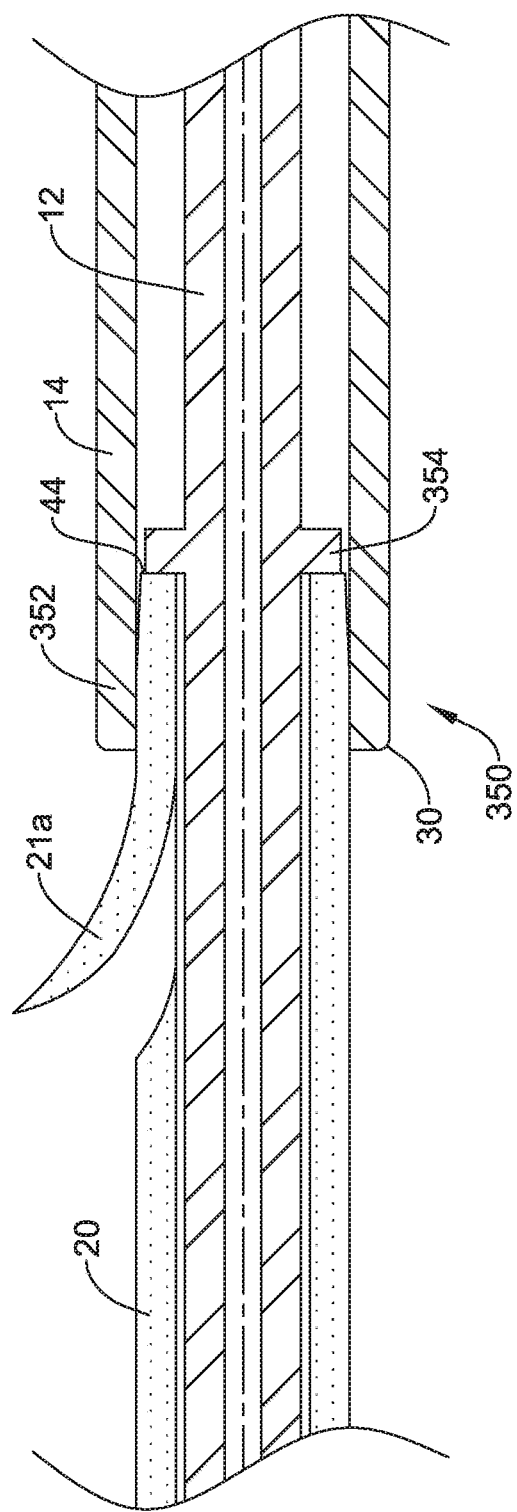
FIGS. 6A-6C are longitudinal cross-sectional views illustrating the functionality of another retention structure for selectively coupling a stent to an elongate shaft of a delivery system.
Figure 6B:
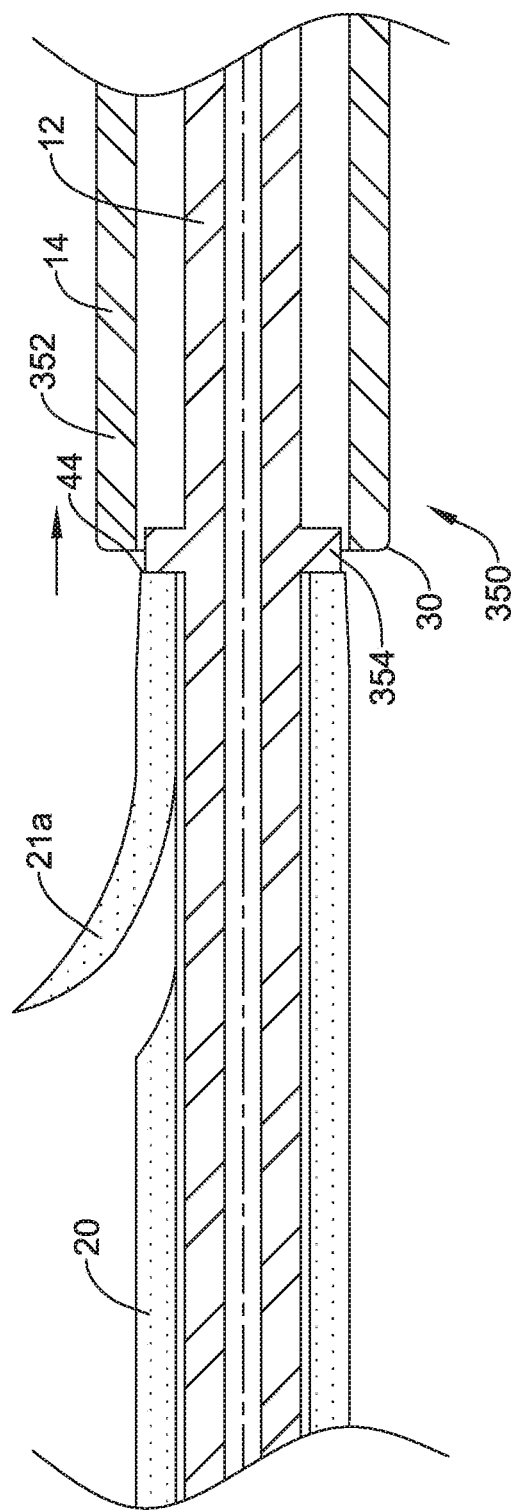
Figure 6C:
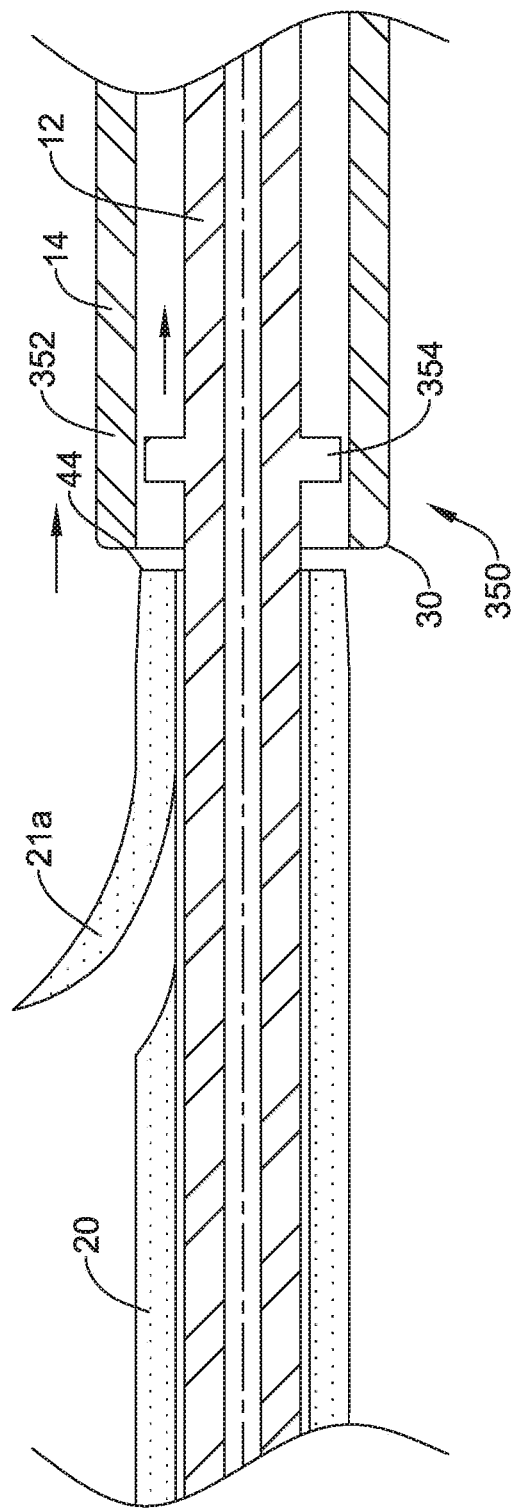

FIGS. 6A-6C illustrate the functionality of yet another exemplary retention structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the drainage stent 20 may be selectively coupled to the guide catheter 12, or another elongate shaft, in the manner described with regard to FIGS. 6A-6C.

FIG. 6A illustrates a distal portion 352 of the push catheter 14 positioned on and surrounding a proximal portion of the drainage stent 20 to retain the drainage stent 20 to the drainage stent delivery system 10. Thus, when coupled to the drainage stent 20, the distal end 30 of the push catheter 14 may be located distal of the proximal end 44 of the drainage stent 20. Also shown in FIG. 6A, a distal portion of the guide catheter 12 may extend distally from the distal end 30 of the push catheter 14 into and/or through the lumen 48 of the drainage stent 20 such that the distal end of the guide catheter 12 is located distal of the proximal end 44 of the drainage stent 20.

The distal portion 352 of the push catheter 14 may be configured to form an interference fit with the drainage stent 20. For instance, the distal portion 352 of the push catheter 14 may be considered an interference fit member 350 configured to cooperate with the drainage stent 20 to form an interference fit therebetween. In some instances, as shown in FIG. 6A, the distal portion 352 of the push catheter 14 may circumferentially surround and be press fit against the outer surface of the proximal portion of the drainage stent 20, forming an interference fit therebetween. The distal portion 352 forming the interference fit member 350 may be a unitary portion of the elongate shaft of the push catheter 14, or the distal portion 352 may be a separate component secured to the elongate shaft of the push catheter 14.

The distal portion 352 may be configured to form an interference fit with a proximal portion of the drainage stent 20 to selectively retain the drainage stent 20 to the push catheter 14 until deployment of the drainage stent 20 is desired. For example, the proximal portion of the drainage stent 20 may be press fit into the distal portion 352 such that the outer surface of the drainage stent 20 presses against the interior surface of the distal portion 352, forming an interference fit therebetween. For instance, the interference fit may be a frictional fit between the interior surface of the distal portion 352 and the exterior surface of the drainage stent 20 having a coefficient of static friction sufficient to retain the drainage stent 20 in the push catheter 14 until deployment is desired. In some instances, the distal portion 352 of the push catheter 14 may be radially compressed or crimped around the proximal portion of the drainage stent 20 by mechanical means to provide a press fit between the distal portion 352 and the drainage stent 20. In some embodiments, the outer diameter of the proximal portion of the drainage stent 20 may be greater than the inner diameter of the distal portion 352 to create an interference fit therebetween.

In a first position, shown in FIG. 6A, in which the proximal portion of the drainage stent 20 is press fit within the distal portion 352 of the push catheter 14, the drainage stent 20 is secured to the push catheter 14. Compressive forces between the inner surface of the distal portion 352 and the exterior surface of the drainage stent 20 provides an interference frictional fit. The interference frictional fit between the distal portion 352 and the drainage stent 20 prevents decoupling of the drainage stent 20 from the push catheter 14 without applying a threshold amount of force to overcome the interference fit.

The drainage stent 20 may be decoupled from the push catheter 14 through axial movement of the push catheter 14 relative to the drainage stent 20. For instance, as shown in FIG. 6B, axial or longitudinal movement of the push catheter 14 in a proximal direction while holding the drainage stent 20 stationary may move the distal portion 352 from the first position in which the distal portion 352 surrounds the proximal portion of the drainage stent 20 to a second position in which the distal portion 352 is positioned proximal of the drainage stent 20.

As shown in FIG. 6B, the guide catheter 12 may be utilized to restrain the drainage stent 20 from proximal movement as the push catheter 14 is withdrawn proximally. For instance, the guide catheter 12 may include an annular rim or projection 354 which contacts the proximal end 44 of the drainage stent 20. The guide catheter 12 may be held stationary as the push catheter 14 is actuated proximally, thereby preventing the drainage stent 20, abutting the annular rim 354 of the guide catheter 12, from moving proximally with the push catheter 14. Alternatively, the guide catheter 12 may be actuated distally while holding the push catheter 14 stationary to expel the proximal portion of the drainage stent 20 distally from the distal portion 352 of the push catheter 14.

An axial force greater than a threshold level is necessary to overcome the coefficient of static friction caused by the interference frictional fit between the distal portion 352 of the push catheter 14 and the exterior surface of the drainage stent 20 a sufficient amount to allow the proximal portion of the drainage stent 20 to be decoupled from the lumen of the distal portion 352 of the push catheter 14. For instance, the distal portion 352 may be sized and configured relative to the outer diameter of the drainage stent 20 such that an axial force of less than 2 pounds applied to the push catheter 14 is insufficient to pull the distal portion 352 proximally from the engagement with the drainage stent 20. The distal portion 352 may be sized and configured such that an axial force greater than 2 pounds, for example, an axial force of about 3 pounds to about 4 pounds, may be sufficient to overcome the coefficient of static friction between the distal portion 352 and the exterior surface of the drainage stent 20 to allow the proximal portion of the drainage stent 20 to be removed from the interior of the distal portion 352 of the push catheter 14. The threshold level of force needed to withdraw the push catheter 14 from the drainage stent 20, and thus decouple the drainage stent 20 from the push catheter 14 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, axial force applied to the push catheter 14 pulls the proximal end 44 of the drainage stent 20 into contact with the annular rim 354 of the guide catheter 12 as the distal portion 352 is frictionally engaged and stationary with the drainage stent 20. When a sufficient axial force is applied to overcome the static frictional force between the distal portion 352 of the push catheter 14 and the drainage stent 20, the distal portion 352 of the push catheter 14 is pulled proximally relative to the drainage stent 20 to a position proximal of the drainage stent 20. Thus, the axial force applied to withdraw the push catheter 14 from the drainage stent 20 must be sufficiently large to overcome the static frictional forces caused by the interference fit between the distal portion 352 and the exterior surface of the drainage stent 20.

As shown in FIG. 6C, once the drainage stent 20 has been decoupled from the distal portion 352 of the push catheter 14, the guide catheter 12 can be withdrawn proximally from the lumen 48 of the drainage stent 20 to deploy the drainage stent 20 at a desired anatomical location. The push catheter 14 may also be withdrawn further proximally simultaneously or consecutively with the guide catheter 12.

Figure 7A:
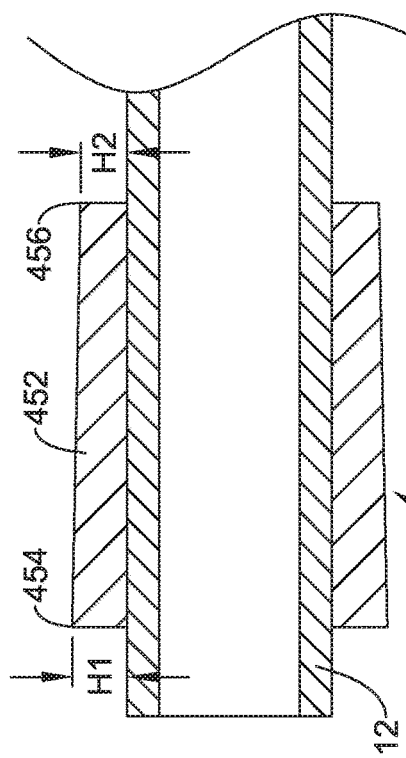
FIG. 7A is a longitudinal cross-sectional view illustrating one possible configuration of an interference fit member.

FIG. 7A illustrates another embodiment of an interference fit member 450 in accordance with this disclosure. It is noted that the configuration of the interference fit member 450 may be incorporated into any one of the other embodiments disclosed herein. The interference fit member 450, located on a distal portion of the guide catheter 12, may be configured to engage the inner surface of the drainage stent 20 to secure the drainage stent 20 on the guide catheter 12.

The interference fit member 450 may include one or more elongate members 452. In some instances, the elongate member 452 may be an annular sleeve surrounding the guide catheter 12. In other instances, one or more elongate members 452 may be located at discrete positions around the circumference of the guide catheter 12 such the elongate members 452 are discontinuous with one another. The elongate member(s) 452 may have a distal end 454 extending a first height H1 (e.g. radially outward) from the outer surface of the guide catheter 12 and a proximal end 456 extending a second height H2 (e.g., radially outward) from the outer surface of the guide catheter 12. The first height H1 may be greater than the second height H2 such that the outer extent of the elongate member(s) 452 tapers relative to the central longitudinal axis of the guide catheter 12. Such a configuration may facilitate removal of the interference fit member 450 from within the drainage stent 20.

In other embodiments, the proximal end of the elongate member 452 may extend radially outward from the outer surface of the guide catheter 12 less than the distal end of the elongate member 452. Such a configuration may facilitate inserting the interference fit member 450 into the lumen of the drainage stent 20, to load the drainage stent 20 on the delivery system.

Figure 7B:
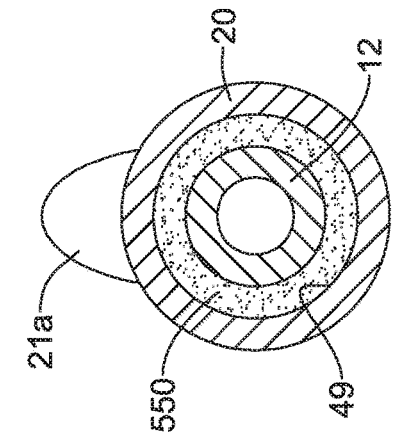
FIGS. 7B-7D are cross-sectional views illustrating possible configurations of an interference fit member engaged with a drainage stent.

FIG. 7B illustrates an embodiment of an interference fit member 550 in accordance with this disclosure. It is noted that the configuration of the interference fit member 550 may be incorporated into any one of the other embodiments disclosed herein. The interference fit member 550, located on a distal portion of the guide catheter 12, may be configured to engage the inner surface 49 of the drainage stent 20 to secure the drainage stent 20 on the guide catheter 12.

The interference fit member 550 may be an annular member circumferentially surrounding the guide catheter 12. Thus, the interference fit member 550 may engage the inner surface 49 of the drainage stent 20 along substantially the entire or the entire circumference of the inner surface 49 of the drainage stent 20.

Figure 7C:
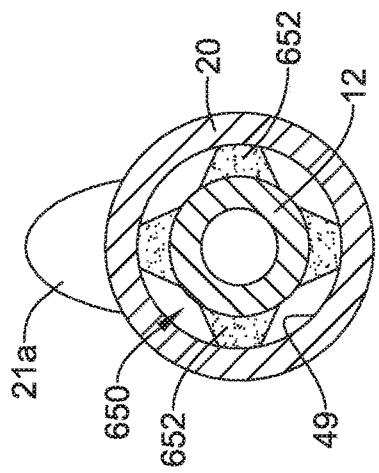

FIG. 7C illustrates an embodiment of an interference fit member 650 in accordance with this disclosure. It is noted that the configuration of the interference fit member 650 may be incorporated into any one of the other embodiments disclosed herein. The interference fit member 650, located on a distal portion of the guide catheter 12, may be configured to engage the inner surface 49 of the drainage stent 20 to secure the drainage stent 20 on the guide catheter 12.

The interference fit member 650 may be one or more discrete and/or discontinuous members 652 positioned symmetrically or asymmetrically around the circumference of the guide catheter 12 and extending radially outward therefrom. Thus, the interference fit member 650 may engage the inner surface 49 of the drainage stent 20 at one or more discrete contact locations around the circumference of the inner surface 49 of the drainage stent 20.

Figure 7D:
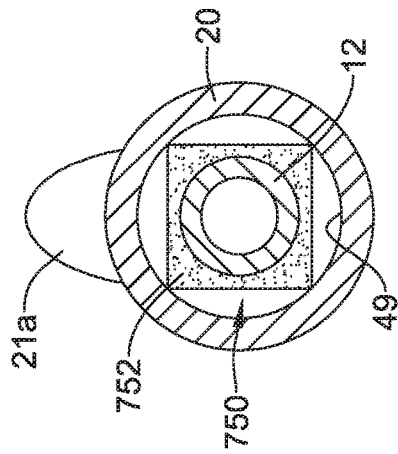

FIG. 7D illustrates an embodiment of an interference fit member 750 in accordance with this disclosure. It is noted that the configuration of the interference fit member 750 may be incorporated into any one of the other embodiments disclosed herein. The interference fit member 750, located on a distal portion of the guide catheter 12, may be configured to engage the inner surface 49 of the drainage stent 20 to secure the drainage stent 20 on the guide catheter 12.

The interference fit member 750 may be a non-circular or polygonal shaped member 752 having one or more portions extending radially outward from the central longitudinal axis of the guide catheter 12 further than other portions of the member 752. For example, as shown in FIG. 7D, the member 752 may have four corners which extend further radially outward than other portions of the member 752. In other instances, the member 752 may have 1, 2, 3, 4, 5, 6, 7, 8 or more corners or edges which extend further radially outward than other portions of the member 752. Thus, the interference fit member 750 may engage the inner surface 49 of the drainage stent 20 at one or more discrete contact locations (e.g., at the corners or edges) around the circumference of the inner surface 49 of the drainage stent 20.

In any of the embodiments disclosed herein, the interference fit member may include a coating or layer to increase friction between the interference fit member and the drainage stent 20 and/or the engaging surface of the interference fit member may be modified to increase friction between the interference fit member and the drainage stent 20. For instance, the interference fit member may include a sticky or tacky coating, a silicone layer, knurlings, bumps, grooves, ridges, surface roughenings, etc., to increase the friction between the interference fit member and the drainage stent 20.

In any of the embodiments disclosed herein, the interference fit member may include a coating and/or be formed of a material which becomes more lubricious when wetted with a fluid. For example, when deployment of the drainage stent 20 is desired, a fluid may be injected through the drainage stent delivery system 10 or through another medical device to reduce the friction between the interference fit member and the drainage stent 20 to facilitate removal of the drainage stent 20 from the interference fit member. Such a fluid may increase the lubricity of the coating and/or material and thus reduce the coefficient of friction between the interference fit member and the drainage stent 20. In some instances regardless of whether such a coating and/or material is used, it still may be desirable to inject a fluid through the drainage stent delivery system 10 or through another medical device during deployment of the drainage stent 20 to facilitate disengagement of the drainage stent 20 from the interference fit member.

In any of the embodiments disclosed herein, the interference fit member may include cuts and/or gaps in the interference fit member which facilitate removal of the interference fit member from the drainage stent 20. For example, such cuts and/or gaps may enhance the flexibility of the interference fit member to deflect, compress, elongate, or otherwise deform as the interference fit member is removed form the drainage stent 20.

Although several illustrated embodiments of the disclosed stent retention structures are illustrated as being incorporated into a delivery system for delivering a drainage stent, it is understood that the stent retention structures may also be used to selectively couple other stent or endoprosthesis devices to a delivery system. For example, in some instances the stent retention structures described herein may be used to selectively couple a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system, comprising:
    a stent including a generally non-expandable tubular member having a proximal end, a distal end and a central longitudinal axis, wherein the proximal end of the stent includes a radially inward extending lip;
    an elongate shaft extending distally from a handle assembly to a location proximal of the proximal end of the stent;
    an inner elongate member extending through a lumen of the elongate shaft and a lumen of the stent, wherein the inner elongate member includes a projection configured to form an interference fit with the lip;
    wherein the inner elongate member is longitudinally moveable from a first position in which the projection is distal to the lip, to a second position in which the projection is proximal to the lip to effect disengagement of the stent from the elongate shaft; and
    wherein the lip defines an opening having a diameter that is smaller than a diameter of the projection.

2. The stent delivery system of claim 1, wherein a distal end of the elongate shaft abuts a proximal end of the stent.

3. The stent delivery system of claim 1, wherein the inner elongate member is longitudinally moveable from a first position in which the projection is within the lumen of the stent and a second position in which the projection is proximal to the stent.

4. The stent delivery system of claim 1, wherein the projection comprises a raised protuberance, annular ridge, annular rim, bump or bulge.

5. The stent delivery system of claim 1, wherein the handle assembly includes an actuator configured to longitudinally actuate the inner elongate member relative to the elongate shaft.

6. A stent delivery system, comprising:
    a handle assembly;
    a non-expandable stent having a proximal end, a distal end and a lumen extending therethrough, wherein the proximal end of the stent includes a radially inward extending lip;
    a push catheter extending distally from the handle assembly, the push catheter having a lumen extending therethrough;
    a guide catheter positioned in the lumens of the push catheter and stent;
    wherein the guide catheter includes a projection configured to form an interference fit with the lip;
    wherein the guide catheter is longitudinally moveable from a first position in which the projection is distal to the lip, to a second position in which the projection is proximal to the lip to effect disengagement of the stent from the push catheter; and
    wherein one of the lip or projection is configured deform upon contact with the other one of the lip or projection as the guide catheter moves from the first position to the second position.

7. The stent delivery system of claim 6, wherein a distal end of the push catheter abuts a proximal end of the stent.

8. The stent delivery system of claim 6, wherein the guide catheter is longitudinally moveable from a first position in which the projection is within the lumen of the stent and a second position in which the projection is proximal to the stent.

9. The stent delivery system of claim 6, wherein the projection comprises a raised protuberance, annular ridge, annular rim, bump or bulge.

10. The stent delivery system of claim 6, wherein the handle assembly includes an actuator configured to longitudinally actuate the guide catheter relative to the push catheter.

11. A stent delivery system, comprising:
    a stent including a generally non-expandable tubular member having a proximal end, a distal end and a central longitudinal axis, wherein the proximal end of the stent includes a radially inward extending lip;
    an elongate shaft extending distally from a handle assembly to a location proximal of the proximal end of the stent;
    an inner elongate member extending through a lumen of the elongate shaft and a lumen of the stent, wherein the inner elongate member includes a projection configured to form an interference fit with the lip;
    wherein the inner elongate member is longitudinally moveable from a first position in which the projection is distal to the lip, to a second position in which the projection is proximal to the lip to effect disengagement of the stent from the elongate shaft; and
    wherein one of the lip or projection is configured to deform upon contact with the other one of the lip or projection as the inner elongate member moves from the first position to the second position.

12. The stent delivery system of claim 11, wherein a distal end of the elongate shaft abuts a proximal end of the stent.

13. The stent delivery system of claim 11, wherein the inner elongate member is longitudinally moveable from the first position in which the projection is within the lumen of the stent to the second position in which the projection is proximal to the stent.

14. The stent delivery system of claim 11, wherein the projection comprises a raised protuberance, annular ridge, annular rim, bump or bulge.

15. The stent delivery system of claim 11, wherein the handle assembly includes an actuator configured to longitudinally actuate the inner elongate member relative to the elongate shaft.

* * * * *